United States Patent
Grinberg et al.

(10) Patent No.: US 9,456,827 B2
(45) Date of Patent: *Oct. 4, 2016

(54) INSTRUMENT FOR IMAGE GUIDED APPLICATIONS

(71) Applicant: DePuy Synthes Products, Inc., Raynham, MA (US)

(72) Inventors: Alexander Grinberg, Auburndale, MA (US); Michael J O'Neil, West Barnstable, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/711,222

(22) Filed: May 13, 2015

(65) Prior Publication Data
US 2015/0245845 A1    Sep. 3, 2015

Related U.S. Application Data
(63) Continuation of application No. 12/817,639, filed on Jun. 17, 2010, now Pat. No. 9,050,108.

(51) Int. Cl.
| | |
|---|---|
| *A61B 17/16* | (2006.01) |
| *A61B 17/88* | (2006.01) |
| *A61B 1/00* | (2006.01) |
| *A61B 17/00* | (2006.01) |

(52) U.S. Cl.
CPC ....... *A61B 17/1622* (2013.01); *A61B 1/00064* (2013.01); *A61B 17/16* (2013.01); *A61B 17/1631* (2013.01); *A61B 17/1633* (2013.01); *A61B 17/88* (2013.01); *A61B 1/00066* (2013.01); *A61B 17/1615* (2013.01); *A61B 17/1655* (2013.01); *A61B 17/8875* (2013.01); *A61B 34/20* (2016.02); *A61B 2017/0042* (2013.01)

(58) Field of Classification Search
None
See application file for complete search history.

(56) References Cited

U.S. PATENT DOCUMENTS

| | | |
|---|---|---|
| 5,769,861 A | 6/1998 | Vilsmeier |
| 5,771,760 A | 6/1998 | Tiede |
| 5,778,743 A | 7/1998 | Tiede |
| 5,848,680 A | 12/1998 | Rinner |
| 5,873,288 A | 2/1999 | Gauthier |
| 5,943,755 A | 8/1999 | Gauthier |
| 6,021,343 A | 2/2000 | Foley |
| 6,190,395 B1 | 2/2001 | Williams |
| 6,428,547 B1 | 8/2002 | Vilsmeier |
| 6,461,356 B1 | 10/2002 | Patterson |
| 6,887,247 B1 | 5/2005 | Couture |

(Continued)

FOREIGN PATENT DOCUMENTS

WO    WO 99/26549    *    6/1999 ............ A61B 19/00

*Primary Examiner* — Katherine Fernandez
*Assistant Examiner* — Michael Kellogg (57) ABSTRACT

A trackable medical instrument for use in a computer assisted image guided surgery system having a digitizer for tracking the position of the instrument in three dimensional space and a display providing an indication of the position of the instrument with respect to images of a body part taken preoperatively, wherein the instrument comprises a tracking array located distally of a rotatable, axially fixed drive handle.

14 Claims, 5 Drawing Sheets

(56) References Cited

U.S. PATENT DOCUMENTS

| | | |
|---|---|---|
| 7,014,023 B1 | 3/2006 | Gauthier |
| 7,156,216 B2 | 1/2007 | Gauthier |
| 7,226,456 B2 | 6/2007 | O'Neil |
| 7,302,355 B2 | 11/2007 | Jansen |
| RE43,328 E * | 4/2012 | Foley .................... A61B 17/16 600/407 |
| 8,239,001 B2 | 8/2012 | Verard |
| 2003/0181918 A1 | 9/2003 | Smothers |
| 2003/0236447 A1 | 12/2003 | Ritland |
| 2004/0092928 A1 | 5/2004 | Sasso |
| 2004/0097804 A1 | 5/2004 | Sobe |
| 2004/0127888 A1* | 7/2004 | O'Neil ............... A61B 17/1622 606/1 |
| 2004/0162559 A1 | 8/2004 | Arramon |
| 2005/0074304 A1 | 4/2005 | Couture |
| 2005/0075562 A1 | 4/2005 | Szakelyhidi |
| 2005/0085715 A1 | 4/2005 | Dukesherer |
| 2005/0113659 A1 | 5/2005 | Pothier |
| 2006/0167461 A1 | 7/2006 | Hawkins |
| 2006/0271056 A1 | 11/2006 | Terrill Grisoni |
| 2007/0172803 A1 | 7/2007 | Hannaford |
| 2007/0270685 A1 | 11/2007 | Kang |
| 2008/0308600 A1 | 12/2008 | Kana |
| 2008/0319313 A1 | 12/2008 | Boivin |
| 2009/0030437 A1 | 1/2009 | Houser |
| 2009/0118742 A1* | 5/2009 | Hartmann .......... A61B 17/1703 606/130 |
| 2009/0306499 A1 | 12/2009 | Van Vorhis |
| 2011/0313281 A1 | 12/2011 | Grinberg |
| 2011/0319898 A1 | 12/2011 | O'Neil |
| 2013/0006270 A1 | 1/2013 | Schmoll |

* cited by examiner

INSTRUMENT FOR IMAGE GUIDED APPLICATIONS

CONTINUING DATA

This patent application claims priority from co-pending patent application U.S. Ser. No. 12/817,639, filed Jun. 17, 2010, entitled "Instrument for Image Guided Applications" (Grinberg), the specification of which is incorporated by reference in its entirety.

BACKGROUND OF THE INVENTION

Computer assisted image guided medical and surgical navigation systems are known and used to generate images in order to guide a doctor during a medical procedure. See, for example, U.S. Pat. Nos. 5,769,861 & 6,428,547. Such systems frequently include a tracking array that is clamped to the instrument desired to be tracked.

U.S. Pat. No. 6,190,395 ("Williams") discloses an IGS system having a flexible clamping band used to attach the tracking array to the instrument.

U.S. Pat. No. 6,021,343 ("Foley '343") discloses a tool for use in image guided surgery comprising an annular guide member having a trackable array and a drive shaft for rotating an instrument such as a screwdriver while keeping the array stationary. In particular, Foley discloses a trackable medical instrument for use in a computer assisted image guided surgery system having a digitizer for tracking the position of the instrument in three dimensional space and a display providing an indication of the position of the instrument with respect to images of a body part taken preoperatively, the instrument comprising: a) a guide member having a tracking device mounted thereon for being tracked by a digitizer; b) a drive shaft contained within the guide member, the drive shaft having a longitudinal axis and a proximal and a distal end, the drive shaft being rotatable within the guide member while being fixable within the guide member in a direction of the longitudinal axis; c) an instrument tip extending from the proximal end of the drive shaft; wherein the instrument tip rotates freely relative to the guide member while being fixable axially relative to the guide member; and d) a drive handle extending from the distal end of the drive shaft for guiding the instrument, including the guide member, and for imparting rotary motion to the drive shaft and the instrument tip independent of the guide member. In each embodiment disclosed in Foley '343, the drive shaft is received within an annulus of the guide member. That is, the annulus of the guide member surrounds the drive shaft, thereby allowing the array to rotate fully around the drive shaft.

Further, Foley '343 discloses attaching the instrument to the drive shaft by a simple male-female socket, in particular a ball-and-detent mechanism. The ball and detent feature of this socket produces considerable error in tracking because the attachment occurs on one side of the connection and so is not substantially radially uniform.

SUMMARY OF THE INVENTION

The present invention relates to a trackable medical instrument for use in a computer assisted image guided surgery system having a digitizer for tracking the position of the instrument in three dimensional space and a display providing an indication of the position of the instrument with respect to images of a body part taken preoperatively, wherein the instrument comprises a tracking array located distally of a rotatable drive handle.

The present invention provides a number of advantages to the surgeon. It can be used with rotatable and stationary instruments without disrupting the screen image. It allows attachment of the tracking array proximal to the drive handle to improve the visibility of the operative site. It also removes the array from the surgical site and minimizes un-intentional rotation of the array onto the patient. The proximal location of the handle provides a more ergonomic solution. The array can be directed attached to the surgeon's hand, thereby obviating the need to hold it manually. Lastly, tracking array of the instrument of the present invention can be easily exchanged for another.

Therefore, in accordance with the present invention, there is provided a trackable medical instrument for use in a computer assisted image guided surgery system having a digitizer for tracking the position of the instrument in three dimensional space and a display providing an indication of the position of the instrument with respect to images of a body part taken preoperatively, the instrument comprising:
a) a guide member having a tracking device mounted thereon for being tracked by the digitizer;
b) a proximal shaft attached to the guide member, the proximal shaft having a longitudinal axis and a proximal end portion and a distal end portion, the proximal shaft being non-rotatable with respect to the guide member while being fixable to the guide member in a direction of the longitudinal axis;
c) a drive handle extending from the distal end portion of the proximal shaft for imparting rotary motion, the drive handle having a proximal end portion and a distal end portion and being rotatable about the distal end portion of the proximal shaft while being fixed with respect to the guide member in a direction of the longitudinal axis;
d) an instrument tip extending from the distal end portion of the drive handle; wherein the instrument tip rotates relative to the guide member while being fixable axially relative to the guide member.

DESCRIPTION OF THE FIGURES

FIG. 1b discloses a longitudinal cross-section of FIG. 1a.

DETAILED DESCRIPTION OF THE INVENTION

Several designs and methods for image guided tracking are disclosed.

Figure 1A:
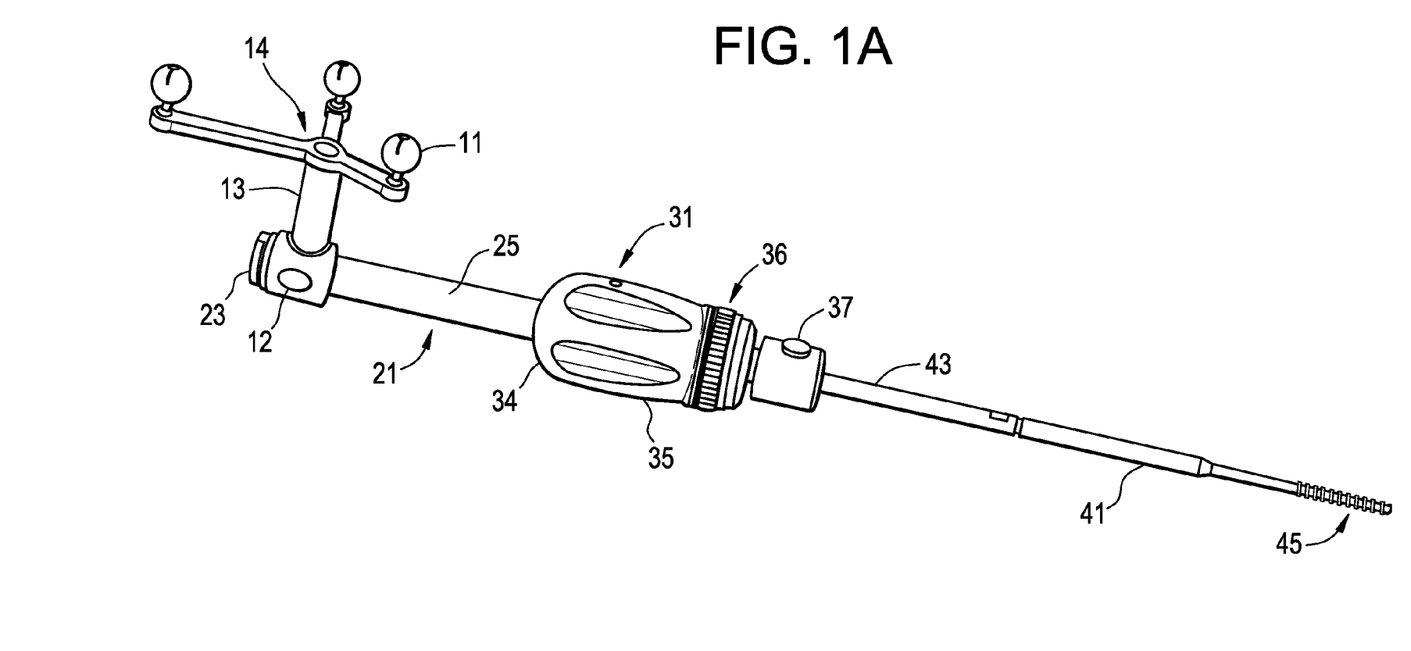
FIG. 1a discloses an instrument of the present invention in which the tracking array is proximal of the rotatable, axially fixed drive handle.
Figure 1B:
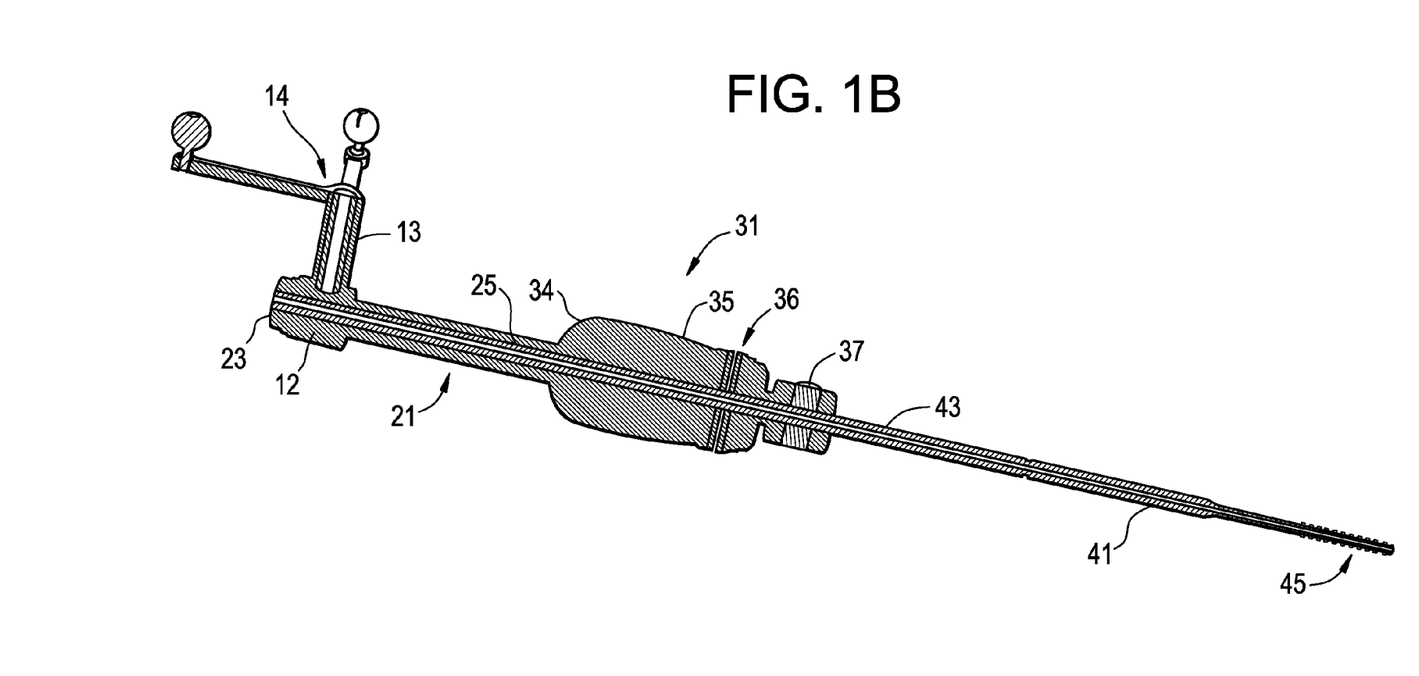

Now referring to FIGS. 1a and 1b, there is provided a trackable medical instrument 1 for use in a computer assisted image guided surgery system having a digitizer for tracking the position of the instrument in three dimensional space and a display providing an indication of the position of the instrument with respect to images of a body part taken preoperatively, the instrument comprising:

a) a guide member 11 comprising a bushing 12, a post 13 and a tracking array 14 mounted thereon for being tracked by a digitizer;

b) a proximal shaft 21 attached to the bushing of the guide member, the proximal shaft having a longitudinal axis, a proximal end portion 23 and a distal end portion 25, the proximal shaft being axially and rotationally fixed with respect to the guide member;

c) a drive handle 31 for imparting rotary motion, the drive handle having a proximal end portion 34 and a distal end portion 35, the drive handle extending from and being rotatable about the distal end portion of the proximal shaft;

d) an instrument tip 41 extending from the distal end portion of the drive handle; the instrument tip having a proximal end portion 43 for insertion into the drive handle and a distal working end portion 45, wherein the instrument tip rotates freely relative to the guide member while being fixable axially relative to the guide member.

The tracking array 14 is attached to the proximal shaft 21 through post 13. Optionally, the guide member further comprises a bushing 12 that is connected to the post and is detachable from the proximal shaft so as to accommodate modular guide members.

The proximal shaft is held and stabilized by the operator's non-dominant hand during instrument rotation and/or advancement to ensure the tracking array is maintained in the line of sight of the IGS tracking system.

The proximal shaft 21 with the attached array can freely rotate within the drive handle, but is fixed axially with respect to the drive handle. Typically, a sleeve having a bore is disposed within the distal end portion of the drive handle, and the distal end portion of the proximal shaft is inserted into that bore, thereby allowing the drive handle to rotate freely about the proximal shaft.

A surgical instrument tip 41 is attached to the distal end portion of the handle. Typically, the instrument tip is selected from the group consisting of a probe, a drill, and a tap. In use, the surgeon may rotate the instrument tip by gripping the drive handle with his/her dominant hand and rotating the drive handle. If either the probe or any non-rotational instruments is used, the guide member may be replaced with an optional guide member that can be locked in the handle to prevent its rotation relative to the handle. The ratchet in this case should be in neutral position.

As shown in FIG. 1A, the distal end portion of the drive handle optionally includes a ratchet mechanism 36. The ratchet mechanism can typically be set to any of three positions. In the first position, which is neutral, the ratchet and the drive handle do not rotate with respect to each other. In this position, simply rotating the drive handle in a first direction rotates the instrument tip in that first direction. This position may be used in conjunction with non-rotational instruments. In a second position, the ratchet handle can rotate counterclockwise with respect to the drive handle. In a third position, the ratchet handle can rotate clockwise with respect to the drive handle.

In use, the surgeon can use the ratchet in the first (neutral) position in order to for non rotational instruments, or to position into the operative site, to confirm trajectory and to apply load for placement of the instrument and/or device into the tissue. Likewise, the surgeon can use the ratchet in the second position in order to drive the tap or the screw into the bone. It can be rotated clockwise for rotational load application to drive or advance a threaded tap or screw. Lastly, the surgeon can use the ratchet in the third position in order to remove the tap or the screw from the bone. It can rotated counter-clockwise for rotational load application to un-screw a tap or a screw.

As shown in FIG. 1, the distal end portion of the drive handle also optionally includes a modular attachment mechanism 37. This modular attachment mechanism 37 allows the surgeon to quickly change instrument tips. Typically, when both a ratchet and modular attachment are used, the modular attachment is located distal to the ratchet.

Figure 2:
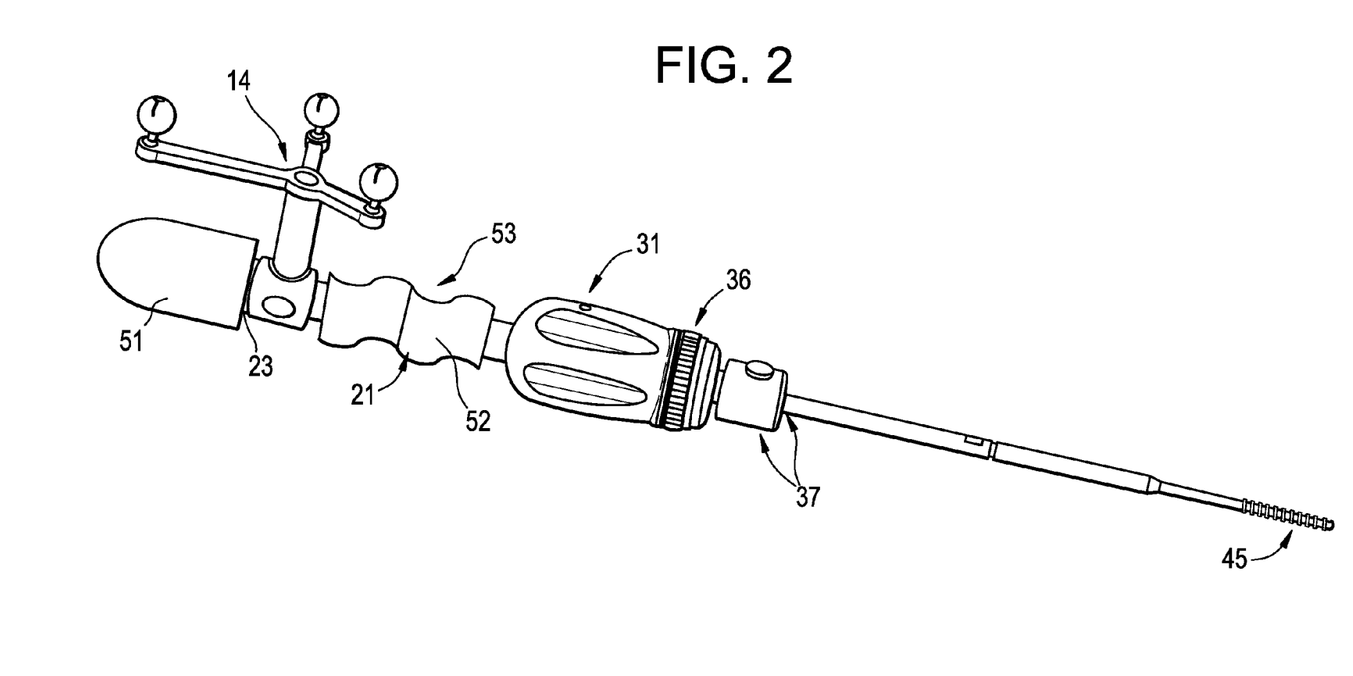
FIG. 2 discloses an embodiment wherein the instrument of FIG. 1a has additional guide handles attached to the proximal shaft on either side of the guide member.

Now referring to FIG. 2, the proximal shaft can include features like second handles 51, 52 which allow the operator to improve stabilization during instrument manipulation. The second handles (or "guide handles") can be located in the mid-portion 53 of the proximal shaft and/or on the proximal end portion 23 of the proximal shaft. The operator typically grasps the guide handle with his/her non-dominant hand. The proximal guide handle, 23, allows for increased axial pressure to be applied by the non-dominant hand.

Figure 3:
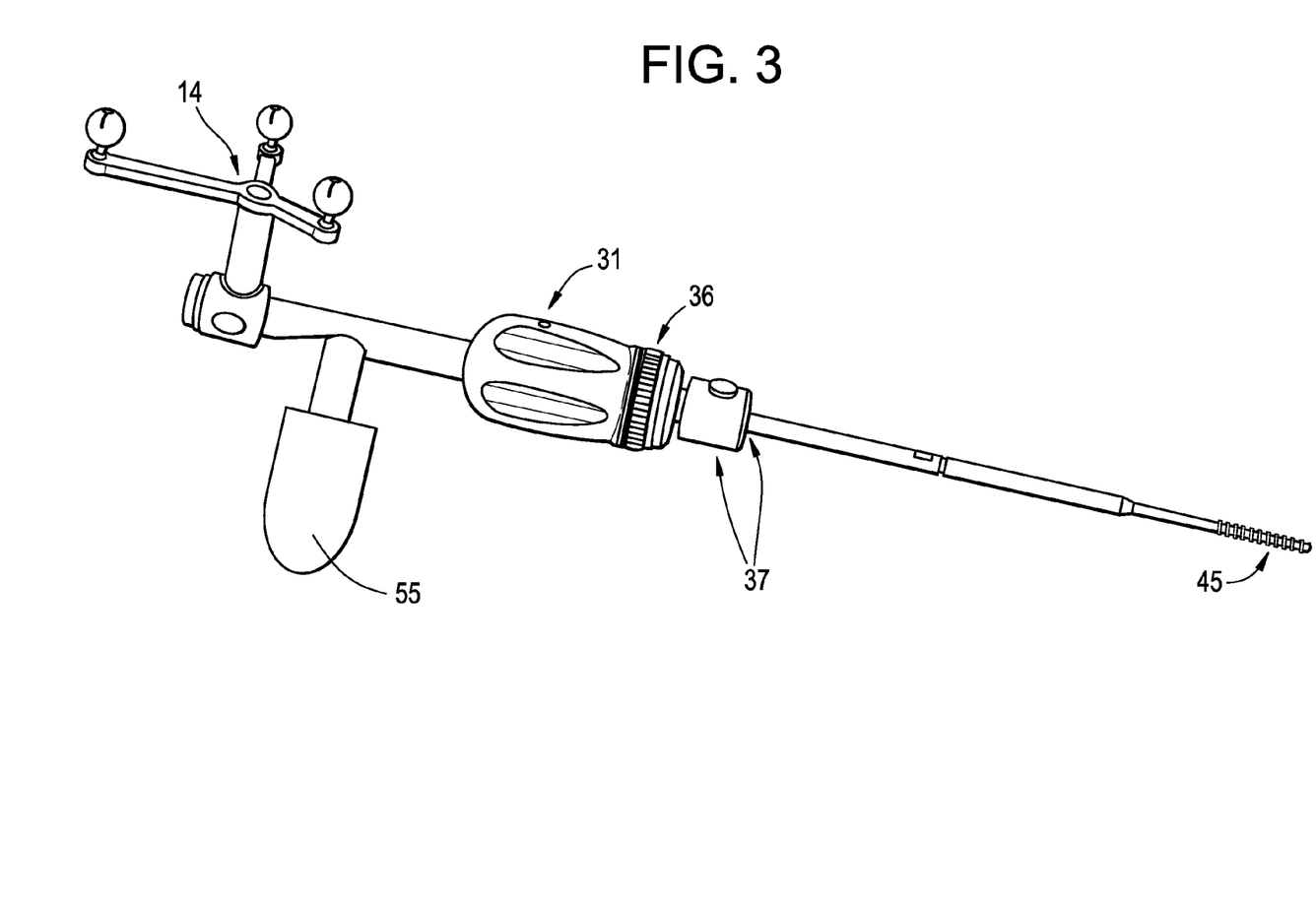
FIG. 3 discloses an embodiment wherein the instrument of FIG. 1a has an additional guide handle extending transversely from the proximal shaft between the guide member and the drive handle.

Now referring to FIG. 3, the proximal shaft with attached tracking array can include a second handle 55 that extends transversely from the proximal shaft. This allows the operator an offset means to hold and secure the tracking array at the desired orientation. This second, offset handle means, 55, also minimizes the likelihood that the non-dominant hand may obscure the array from the detection sensors.

Figure 4:
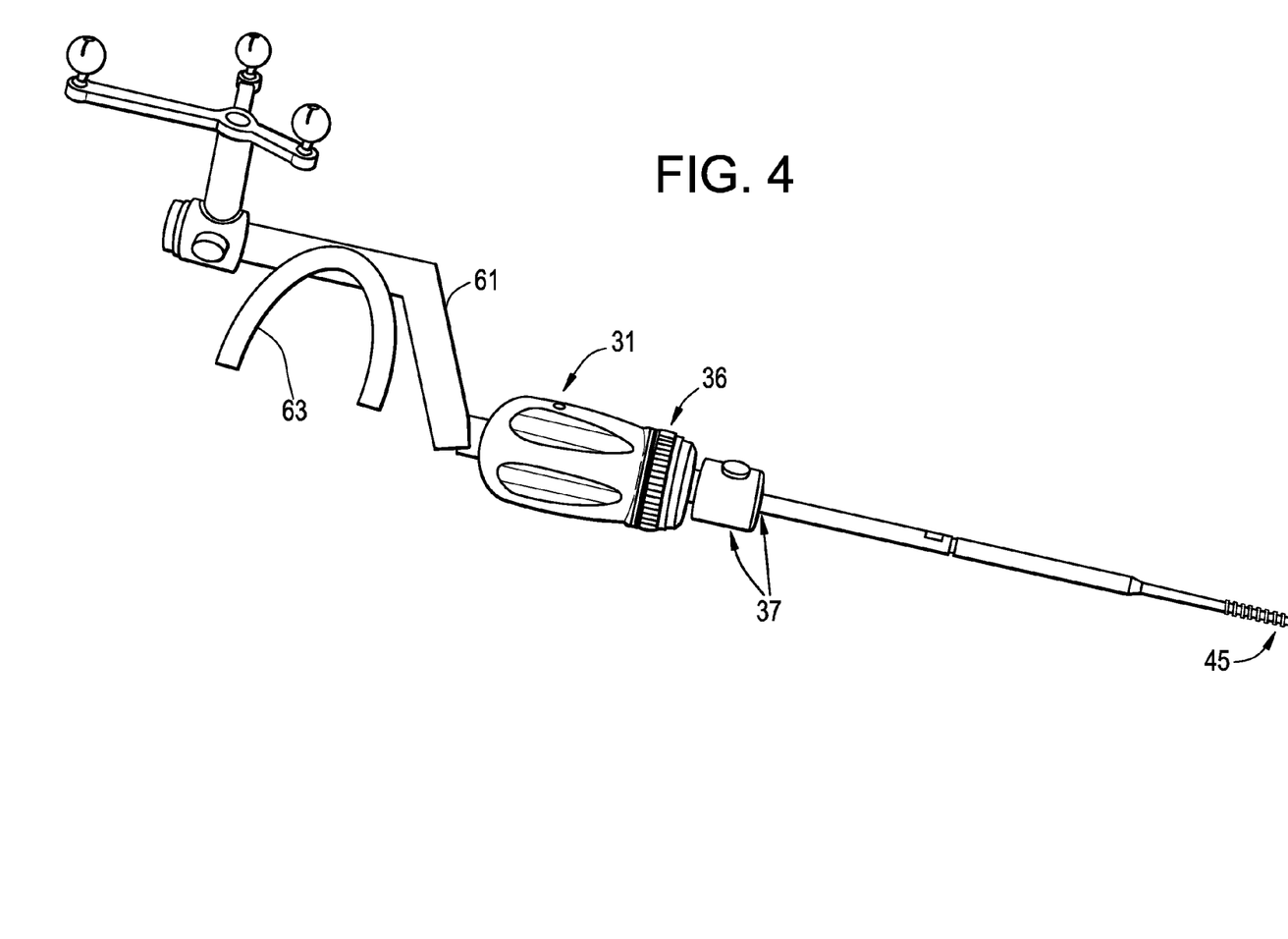
FIG. 4 discloses an embodiment wherein the instrument of FIG. 1a has an additional hand attachment feature located on the proximal shaft.

Now referring to FIG. 4, the portion of the proximal shaft with the attached tracking array can be offset from the longitudinal axis of the drive handle. This is often accomplished by provided an offset proximal shaft 61. The instrument can optionally include a hand attachment feature 63 such as a c-clip or belt means that extends transversely from the offset proximal shaft 61 and securely connects to the operator's arm or hand to ensure the array is maintained in the field of view of the tracking system. This can offer a significant benefit if the drive handle is utilized in the horizontal plane (i.e., placement of posterior hardware with the patient in the lateral position, as it allows the array to maintain vertical orientation during instrument manipulation. Additionally, the c-clip or belt enables single hand use.

Preferably, the instrument of the present invention is typically used in conjunction with a computer-assisted image guided surgery system having i) a digitizer for tracking the position of the instrument in three dimensional space and ii) a display providing an indication of the position of the instrument with respect to images of a body part taken preoperatively. Preferably, the computer tracks the trajectory of the tool and the depth of the instrument inserted into the body part. In some embodiments, the computer-assisted image guided surgery system is that disclosed in U.S. Pat. Nos. 5,769,861 & 6,428,547, the specification of which is incorporated by reference in its entirety.

The function of the drive handle component of the present invention is to transmit torque from the drive handle to the instrument tip. Preferably, the drive handle is fixed axially with respect to the tracking post, the tracking array, and the instrument tip. Preferably, the drive shaft is at least partially rotatable with respect to the tracking array, post and proximal shaft. More preferably, the drive shaft is fully rotatable with respect to the tracking array, post and proximal shaft.

The combination of the tracking post and bushing components of the present invention provides an axially fixed connection between the tracking array and the power train components (i.e., the drive handle and the instrument).

In accordance with the present invention, the instrument includes a tracking device attached to the tracking post for tracking the location and trajectory of the instrument. The tracking device may be equipped with a plurality of tracking means, preferably three tracking means, for generating a signal representing the trajectory of the tool and the depth of the instrument tip. Preferably, the tracking means are passive, and more preferably comprise reflective surfaces. However, other tracking devices that are capable of being tracked by a corresponding sensor array are within the scope of the present invention. For the purposes of illustration, and not limitation, the tracking device may generate signals actively such as with acoustic, magnetic, electromagnetic, radiologic and micropulsed systems, and emitters such as LEDs.

The instrument tip is located at the distal end of the instrument and, when rotated, is able to work upon a body part or implanted device. Preferably, the instrument rotates freely relative to the tracking post. Preferably, the instrument is axially fixed with respect to the tracking post. In some embodiments, the instrument is selected from the group consisting of a screwdriver, an awl, a tap, and a body having a shaped end for mating with a workpiece to be rotated.

The function of the instrument of the present invention is to help the surgeon track the trajectory of a surgical instrument tip placed within the body, thereby enhancing the access and accuracy of the spinal surgery procedure. Preferably, the selected instrument tip can mark, puncture, probe, tap, screw or guide the placement of an implant. Instrument tips are attached to the instrument of the present invention by placing the proximal end portion of the instrument tip into the centering distal coupling means and preferably piloting the proximal end into a recessed 'D' feature of the collet chuck for increased torque. Rotation of the collet nut component of the coupling means both self-centers and secures the instrument. The ratchet mechanism is then adjusted to select rotation options such as non-rotation, right hand drive and left handed drive.

The drive handle imparts rotary motion to the instrument tip. In some embodiments, the drive handle further comprises a ratchet mechanism. In some embodiments, the ratchet mechanism is disposed in the distal end portion of the drive handle. In preferred embodiments, the ratchet mechanisms disclosed in U.S. Pat. Nos. 5,943,755; 5,873,288; 5,848,680; 5,778,743 and 5,771,760, the ratchet mechanism disclosures of which are incorporated by reference, are used. In some embodiments, the ratcheted drive handle is substantially similar to the ratcheted handle disclosed in U.S. Pat. No. 7,014,023, the specification of which is incorporated by reference in its entirety, or in U.S. Pat. No. 7,156,216, the specification of which is incorporated by reference in its entirety.

In preferred embodiments, the proximal end of the instrument tip is coupled to the drive handle by an attachment means (or "coupling means") located in the distal end portion of the drive handle. Preferably, the attachment means provides a self-centered connection of the proximal end of the instrument tip to the distal end portion of the drive handle. In some embodiments, the self-centering coupling means comprises a collet. The collet provides the user with a quick connect/disconnect option by simple hand twisting. The self-centering feature of the collet also provides a more accurate attachment of the instrument to the drive shaft than the ball-and-detent socket disclosed in the Foley '343 patent. In some embodiments, the attachment means comprises a collet, a collet chuck and a collet nut. Preferably, the instrument is inserted through the collet and into the collet chuck. In some embodiments, the transverse cross-section of the distal end of the collet chuck recess has a non-circular shape, such as a D-shaped drive feature. This feature provides enhanced torque transmission. In other embodiments, the attachment means may be a Hudson connection.

In some embodiments, the tool may further comprise a second handle (or "guide handle"), as shown in FIG. 2. The purpose of the second handle is to provide the user with a grippable surface for the non-dominant hand that allows the user to steady or stabilize the instrument while the drive handle is rotated. Preferably, the guide handle has radially extending finger grips (not shown). In some embodiments, the guide handle is attached to an entire circumferential portion of the proximal shaft. This allows for added axial pressure to be administered by the non-dominant hand to the operative site.

In some embodiments the non-dominant handle can be positioned transverse to the drive shaft. See FIG. 3. This helps to keep the non-dominant hand from obscuring the view of the array detection sensors.

In some embodiments the handle can be offset to the drive shaft This can provide a significant benefit if the drive handle is utilized in the horizontal plane (i.e., placement of posterior hardware with the patient in the lateral position, as it allows the array to maintain vertical orientation during instrument manipulation. Additionally, the c-clip or belt enables single hand use.

In some embodiments, the tool further comprises a lock (not shown). The lock prevents rotation of the drive handle vis-a-vis the proximal shaft, and so would be desirable when the surgeon is using a non-rotating instrument such as a probe or an awl. This lock may be provided by an external latch connecting the drive handle and proximal shaft, or by an internally enclosed ratchet mechanism.

The trajectory of the instrument is determined relative to the preoperative CT scan or other imaging data and displayed on the computer screen of the imaging system.

A preferred method with rotary drive instruments (tap or screw) comprises the steps of placing the surgeon's dominant hand on the drive handle and the surgeon's non-dominant hand on the guide handle, with the tracking post typically pointing upright. Rotation is applied to the drive handle with dominant hand while non-dominant hand stabilizes the guide handle. As rotation is imparted, the drive handle rotates around the proximal shaft and torque is transferred to the instrument tip. In some embodiments, rotation of the dominant hand in the opposite direction activates the ratchet mechanism to allow the ratchet to return to its original position and to provide smooth advancement of the surgical instrument while the trajectory image is displayed operatively.

Therefore, in accordance with the present invention, there is provided a method of using a medical instrument in a computer assisted image guided surgery system having a digitizer for tracking the position of the instrument in three dimensional space and a display providing an indication of the position of the instrument with respect to images of a body part taken preoperatively, the method comprising the steps of:

a) selecting an instrument of the present invention,
b) contacting the instrument tip to an implant disposed in the body part.

Also in accordance with the present invention, there is provided a method of using a medical instrument in a computer assisted image guided surgery system having a digitizer for tracking the position of the instrument in three dimensional space and a display providing an indication of the position of the instrument with respect to images of a body part taken preoperatively, the method comprising the steps of:
a) selecting an instrument of the present invention,
b) contacting the instrument tip to the body part.

Typically, the components of the present invention can be made out of any material commonly used in medical instruments. If the device is designed to be reusable, it is preferred that all the components be made of stainless steel. If the device is designed to be disposable, it is preferred that some of the components be made of plastic. Preferably, at least one component is sterilized. More preferably, each component is sterilized.

In some embodiments, the body part upon which the tool of the present invention works is hard tissue. In preferred embodiments, the hard tissue comprises bone. In more preferred embodiments, the body part is a human vertebra. In more preferred embodiments, the tool works upon the posterior portion of the vertebra.

We claim:

1. A trackable medical instrument for use in a computer assisted image guided surgery system having a digitizer for tracking the position of the instrument in three dimensional space and a display providing an indication of the position of the instrument with respect to images of a body part taken preoperatively, the instrument comprising:
   a) a guide member having a tracking device mounted thereon for being tracked by the digitizer;
   b) a proximal shaft attached to the guide member, the proximal shaft having a longitudinal axis and a proximal end portion and a distal end portion, the proximal shaft being non-rotatable with respect to the guide member while being fixable to the guide member in a direction of the longitudinal axis;
   c) a drive handle extending from the distal end portion of the proximal shaft for imparting rotary motion, the drive handle having a proximal end portion and a distal end portion and being rotatable about the distal end portion of the proximal shaft;
   d) an instrument tip extending from the distal end portion of the drive handle; wherein the instrument tip rotates relative to the guide member while being fixable axially relative to the guide member, and
   wherein the drive handle imparts rotary motion to the instrument tip.

2. The instrument of claim 1 wherein the guide member comprises a post, wherein the tracking device is mounted upon the post.

3. The instrument of claim 2 wherein the guide member further comprises a bushing, wherein the post is connected to the bushing.

4. The instrument of claim 3 wherein the bushing is attached to the proximal end portion of the proximal shaft.

5. The instrument of claim 3 wherein the bushing is replaceably attached to the proximal end portion of the proximal shaft.

6. The instrument of claim 1 wherein the proximal shaft has a second handle formed thereon.

7. The instrument of claim 6 wherein the second handle is located between the guide member and the drive handle.

8. The instrument of claim 7 wherein the second handle extends in a direction transverse to the proximal shaft.

9. The instrument of claim 7 wherein the second handle extends in a direction parallel to the proximal shaft.

10. The instrument of claim 7 wherein the proximal shaft is offset from a longitudinal axis of the drive handle.

11. The instrument of claim 1 wherein the proximal portion of the drive handle includes a sleeve having a bore.

12. The instrument of claim 11 wherein the distal portion of the proximal shaft is inserted in the bore of the sleeve of the proximal portion of the drive handle.

13. The instrument of claim 1 wherein the distal portion of the drive handle further comprises a ratchet mechanism.

14. The instrument of claim 1 wherein the instrument tip is selected from the group consisting of a probe, a drill, and a tap.

* * * * *